United States Patent [19]
Lee et al.

[11] Patent Number: 5,569,928
[45] Date of Patent: Oct. 29, 1996

[54] PHOTOACTIVATION LIGHT ARRAY

[75] Inventors: Kyu H. Lee, Bryn Mawr; Livingston B. Morris, Devon; David W. Palmer, deceased, late of Conshohocken, all of Pa., by Susan Palmer, Legal Representative

[73] Assignee: Therakos, Inc, West Chester, Pa.

[21] Appl. No.: 166,494

[22] Filed: Dec. 14, 1993

[51] Int. Cl.$^6$ .................................... A61N 5/06
[52] U.S. Cl. ................... 250/494.1; 250/504 H; 250/455.11; 313/1; 313/493; 362/216
[58] Field of Search ............... 250/494.1, 455.1, 250/504 R; 313/1, 493; 362/216

[56] References Cited

U.S. PATENT DOCUMENTS

| | | | |
|---|---|---|---|
| 2,472,597 | 6/1949 | Levy | 362/216 |
| 2,688,690 | 9/1954 | Lane | 362/216 |
| 2,814,721 | 11/1957 | Fry | 362/216 |
| 4,568,328 | 2/1986 | King | 604/6 |
| 4,573,960 | 3/1986 | Goss | 604/6 |
| 4,573,961 | 3/1986 | King | 604/6 |
| 4,573,962 | 3/1986 | Troutner | 604/6 |
| 4,578,056 | 3/1986 | King et al. | 604/6 |
| 4,681,568 | 7/1987 | Troutner | 604/250 |
| 4,687,464 | 8/1987 | Troutner | 604/4 |
| 4,692,138 | 9/1987 | Troutner et al. | 604/4 |
| 4,705,498 | 11/1987 | Goss | 604/4 |
| 4,708,715 | 11/1987 | Troutner et al. | 604/6 |
| 4,737,140 | 4/1988 | Lee et al. | 604/4 |
| 4,897,789 | 1/1990 | KIng et al. | 364/413.07 |
| 4,915,683 | 4/1990 | Sieber | 604/4 |
| 4,921,473 | 5/1990 | Lee et al. | 494/27 |
| 4,999,375 | 3/1991 | Bachynsky et al. | 514/455 |
| 5,089,384 | 2/1992 | Hale | 435/2 |
| 5,150,705 | 9/1992 | Stinson | 128/396 |

*Primary Examiner*—Jack I. Berman
*Attorney, Agent, or Firm*—John W. Wallen, III

[57] ABSTRACT

Light arrays for use in systems for separating and irradiating blood are disclosed. In accordance with the present invention, the light array has one or more bulbs with electrical connecting leads and first and second support members connected to the bulbs. The second support member preferably includes a connector for receiving the electrical leads. The support members preferably define an end surface and an interior surface, wherein the support members are disposed adjacent the bulbs so the end surfaces are opposed to define a channel, providing a space where tubing carrying blood or other fluids can be disposed without interfering with the array. The bulbs are most preferably attached to the support members using flexible self-locking straps, and in embodiments using two or more bulbs, the bulbs are also preferably held together by one or more straps. Improved mounting systems for connecting the array to the instrument by one or more spring mounts are also disclosed. In certain preferred embodiments, one of the support members is a circuit board and includes a microcircuit for controlling the operation of the array using a clock/timer circuit for determining a total time of activation for the array, whereby upon reaching a predetermined value of the total time of activation, the clock/timer circuit disables the light array. Thus, methods of controlling the output of an array of bulbs are also disclosed.

17 Claims, 3 Drawing Sheets

PHOTOACTIVATION LIGHT ARRAY

The present invention relates to methods and apparatus for extracorporeal blood treatment, and in particular relates to light arrays for exposing blood or blood components to ultraviolet radiation.

BACKGROUND OF THE INVENTION

It is well known that certain human disease states respond favorably to the treatment of certain blood components by visible or ultraviolet irradiation, with or without the introduction of outside agents, compounds or catalysts. For example, it is known that psoralen compounds form photoadducts with DNA in the presence of ultraviolet radiation, thereby moderating the viability of leukocyte populations.

Systems employing these techniques are known whereby extracorporeal treatment of a patient's blood is undertaken. For example, in U.S. Pat. No. 4,573,960—Goss, a patient is given a drug that requires photoactivation and the patient's blood is then withdrawn and separated into its components. The undesired components are returned to the patient. The patient is then disconnected from the treatment apparatus and the separated components, e.g., white blood cells, are exposed to ultraviolet light. Following photoactivation, the treated cells are returned to the patient.

In prior art systems such as those described in the Goss patent, the actual separation of white blood cells from whole blood requires subjective judgement on the part of the operator of a centrifuge, and inevitably results in contamination with some red blood cells. The contamination interferes with the irradiation process and reduces the effectiveness of the treatment. This problem has been largely solved by the methods and apparatus disclosed in U.S. Pat. No. 4,921,473—Lee et al., which is assigned to the assignee of the present invention and is incorporated herein by reference. In the apparatus disclosed in the Lee et al. patent, the fluid to be irradiated is introduced into a sealed chamber. The rotation of the chamber centrifugally separates the fluid into layers and the inner layer or layers are exposed to a light source disposed opposite a transparent inner wall of the chamber. The chamber then ceases rotating, remixing the components of the fluid, and the reconstituted fluid is returned to the patient.

However, although the apparatus disclosed in the Lee et al. patent provides greatly enhanced results, a number of problems exist which, if overcome, would further enhance the effectiveness and efficiency of such systems. It would be desirable, for example, to provide an ultraviolet lamp configuration that provides the highest radiation density against a spinning cylindrical wall. Because the photoactivation treatment should be controlled and repeatable such a lamp configuration should be designed so that it cannot be used after the performance of the lamps has degraded below a certain level. Additionally, because it is necessary to place the lamp assembly within the center of a spinning centrifuge chamber, space is at a premium and the lamp assembly should occupy a minimum envelope and also be able to accommodate variations in bulb dimensions so that conventional commercially available bulbs can be used. Although ultraviolet bulbs are available in standard sizes, the dimensional tolerances are not tightly controlled thus any configuration for retaining standard bulbs in an array must accommodate the dimensional variations in the replacement bulbs.

It would also be desirable to be able to replace the lamp assembly quickly and easily to minimize down time after the lamp assembly has degraded and must be replaced. Conversely, the lamp assembly should be integrated into the equipment so that other normally replaced or renewed components can also be maintained without having to remove the lamp assembly. For example, in certain embodiments of photoactivation equipment it is necessary to replace a disposable irradiation chamber and blood tubing. It would be desirable to be able to undertake such replacement without disconnecting the lamp assembly. Moreover, in certain equipment, it is necessary that tubing carrying the whole blood occupy space within the centrifuge chamber such that the light array could interfere with the tubing as the chamber is opened and closed. Clearly, such interference should be avoided and the structure of the apparatus should protect the blood tubing where possible. Finally, it would also be desirable of the lamp power and signal electronics were connected to the lamps without interfering with the rotation centrifuge chamber.

SUMMARY OF THE INVENTION

It has now been found that systems for separating and irradiating blood that comprise an instrument that includes a rotatable separation and irradiation chamber can be provided with an improved light array that provides a source of radiant energy. In accordance with the present invention the light array has one or more bulbs with electrical connecting leads and at least one support member connected to the bulbs that preferably includes a connector for receiving the electrical leads. In certain preferred embodiments, the support members define an end surface and an interior surface, wherein the support members are disposed adjacent the bulbs so the end surfaces are opposed to define a channel, providing a space where tubing carrying blood or other fluids can be disposed without interfering with the array. The bulbs are most preferably attached to the support members using flexible self-locking straps, and in embodiments using two or more bulbs, the bulbs are also preferably held together by one or more straps.

Improved mounting systems for the array are also disclosed. The disclosed array is preferably connected to the instrument by one or more spring mounts, most preferably three centrally disposed and equally spaced spring mounts that are comprised of leaf springs.

In certain embodiments of the present invention, one of the support members is a circuit board and includes a microcircuit for controlling the operation of the array. Most preferably, the microcircuit comprises a clock/timer circuit for determining a total time of activation for the array, whereby upon reaching a predetermined value of the total time of activation, the clock/timer circuit disables the light array. Thus, the present invention also discloses methods of controlling the output of an array of bulbs.

3

Figure 3:
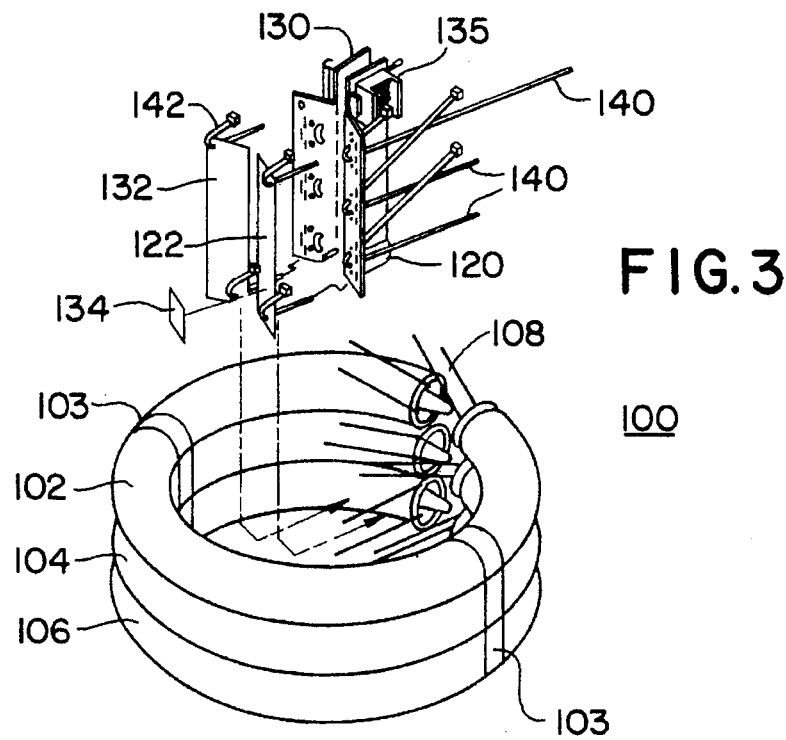
FIG. 3 is an exploded perspective view of the light array and the electrical connectors made in accordance with the present invention.
Figure 4:
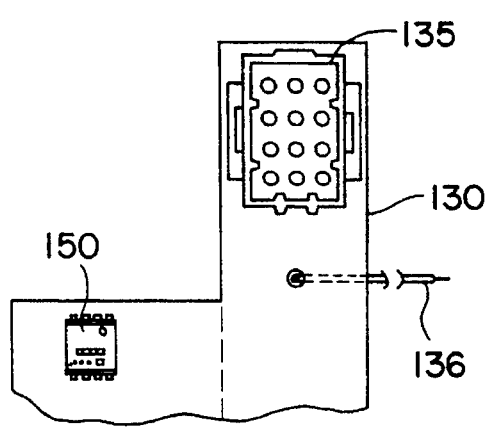
FIG. 4 is a plan view, partially broken away, of the support guide assembly and electrical connector seen in FIG. 3, during its fabrication.
Figure 5:
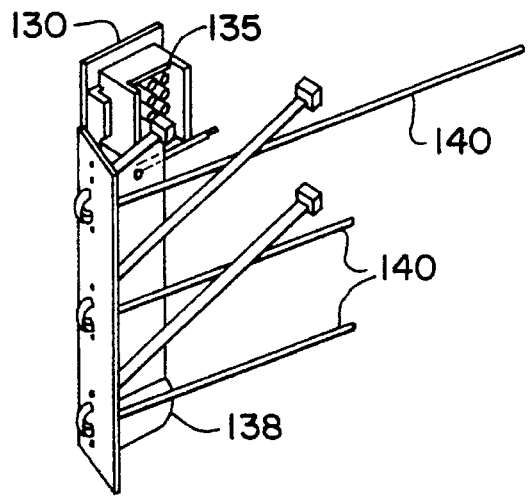

FIG. 5 is a perspective view of the support guide assembly and electrical connector shown in FIGS. 3–4.

Figure 6:
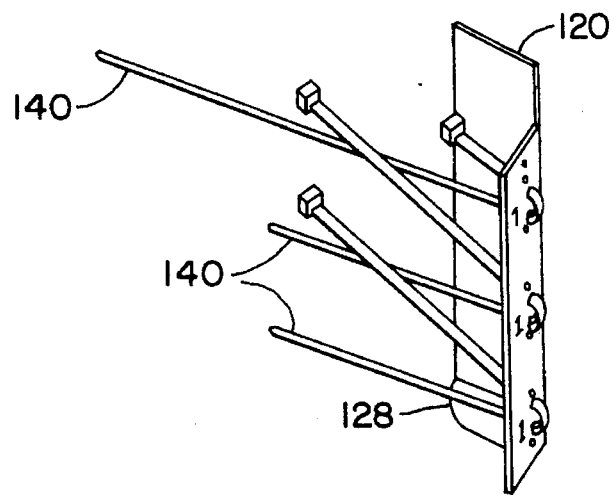

FIG. 6 is a perspective view, similar to FIG. 5, of a support guide assembly seen in FIG. 3.

DETAILED DESCRIPTION OF THE PREFERRED EMBODIMENTS

Figure 1:
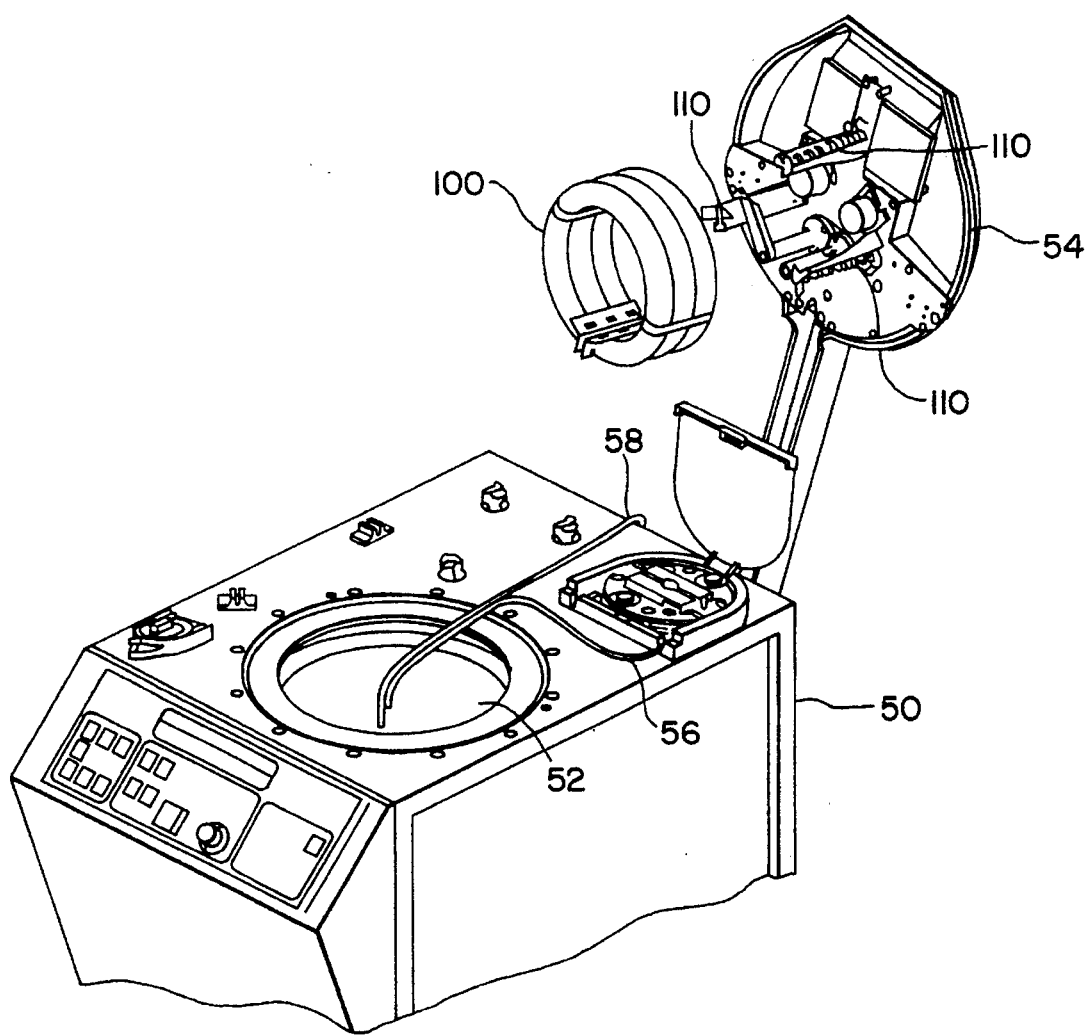
FIG. 1 is a partial perspective view of an apparatus incorporating the light array of the present invention.

Referring to FIG. 1, an exploded perspective view of an instrument 50 that incorporates an array of circular, tubular bulbs 100 made in accordance with the present invention is shown. The array 100 and associated components fit inside the diameter of a cylindrical irradiation chamber 52 that is part of the instrument 50. The construction and operation of the instrument 50 is preferably in accordance with in U.S. Pat. No. 4,921,473—Lee et al., described above and incorporated herein by reference. The array 100 fits within the chamber 52 as closely as possible, thereby maximizing the radiation density falling against the sides of the chamber 52 where the white blood cells are located when the instrument 50 is in operation.

Figure 2:
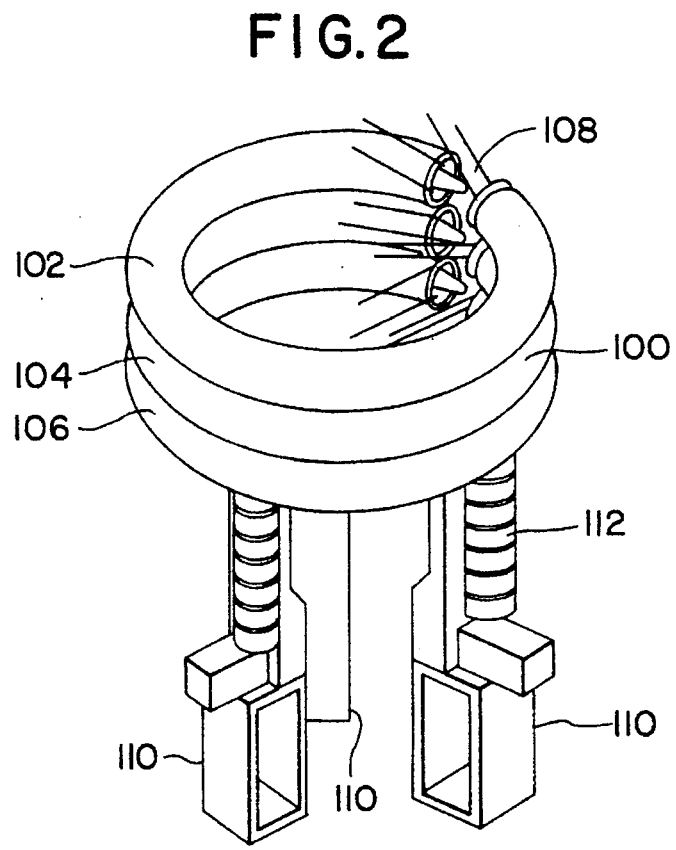
FIG. 2 is a perspective view of a light array and mounting springs made in accordance with a preferred embodiment of the present invention.

As noted above, commercially available ultraviolet bulbs exhibit a relatively wide range of dimensional tolerances and thus, as seen in FIG. 1, preferred embodiments of the present invention provide at least three spring mounts 110 to center each bulb of the array 100 independently. Referring now to FIG. 2, it can be seen that each spring mount 110 includes a leaf spring 112 over which the individual bulbs 102,104, 106 will slide. The flexible fit provided by the leaf springs 112 compensates for the variation in bulb dimensions and also provides a self-centered assembly. Also seen in FIG. 2 are the leads 108 that connect each bulb to a power supply when the apparatus is fully assembled. An advantage of the preferred embodiment of the array 100 disclosed herein is that it uses only three bulbs 102,104,106, whereas the prior systems used as many as 22. However, although the preferred embodiment illustrated uses three bulbs 102,104,106, it will be understood that any number of bulbs can be utilized in an array assembly 100 as shown. Because of the simplicity and reduced number of parts, the array 100 disclosed herein is smaller, lighter and is cheaper to build.

Referring again to FIG. 1, it can be appreciated that the subassembly illustrated in FIG. 2 is affixed to a cover 54 that is preferably hinged to the instrument as shown. When the cover is lifted, the array 100 is also lifted from within the chamber 52, thereby providing access to its interior. The structure should be configured to avoid interference with the blood tubing 56 and vent tubing 58 that cooperate with the irradiation chamber 52 and the rest of the instrument 50 in preferred embodiments.

Further details of the array 100 shown in FIG. 1 are illustrated with reference to FIG. 3. As shown therein, the three bulbs 102,104,106 are loosely held together with straps 103 preferably comprised of vinyl or another flexible material that can withstand the heat and ultraviolet radiation emitted by the bulbs 102,104,106. In accordance with this aspect of the invention, a flexible bulb package is created by tying each bulb loosely to common support members 120, 130. As explained in further detail below, at least one of the support members 120 includes circuit boards and associated electronics that control the operation of the light array 100. In the preferred embodiment illustrated, the support members 120,130 are attached to the bulbs 102,104,106 using flexible self-locking straps 140. Also seen in FIG. 3 are covers 122,132 that overlie the inside surfaces of the support members 120,130, the covers 122,132 are also preferably attached using self-locking straps 142. In certain embodiments, a bar code label 134 or other identifying label may also be affixed to the support members 120,130 as shown.

Referring still to FIG. 3, it can also be seen that the power leads 108 are disposed in the vicinity of the support members 120,130 and in preferred embodiments of the present invention, the leads 108 are inserted into a connector 135 that is attached to one of the support members 130. Details of this aspect of the invention are seen in the broken away portion of the support member 130 shown in FIG. 4. FIG. 4 illustrates the circuit board portion in a "flattened out" configuration that is bent into the configuration illustrated in FIGS. 3 and 5. A wire 136 provides the connection between the connector 135 and a power source. A seen in FIG. 4, the connector 135 is preferably a twelve pin connector since three bulbs 102,104,106 are used in the illustrated embodiment and each bulb has four power leads 108 (as seen in FIG. 3).

FIG. 4 also illustrates a preferred location for the microcircuit 150 that controls the operation of the array 100 of the present invention. The structure of the support member 130 preferably includes or is part of a circuit board that comprises not only the microcircuit 150 illustrated, but other printed circuit lines and devices as required by a particular application. As explained above, because the emissions of ultraviolet bulbs degrade over time, it is desirable to provide a control circuit that monitors the time of use for a light array 100 and, after a predetermined period of time is reached, blocks the power from the array 100 indicating that it must be replaced. In this way, the reliability of the instrument 50 described above is increased since it is now known with certainty that when the light array is operating, the ultraviolet emissions are within a preferred power range and thus effectively irradiate the blood components within the centrifuge chamber 52 shown in FIG. 1.

Thus, in another aspect of the present invention, methods of controlling the output of an array of bulbs are disclosed. The methods of the present invention include the steps of monitoring the total time the bulbs are activated; comparing the total time to a predetermined time value and determining if the total time exceeds the predetermined time value. When the total time exceeds the predetermined time value, the array is disconnected from its power source, indicating the need for replacement.

FIGS. 5–6 provide perspective illustrations of the support members 120,130 and the flexible straps 140 used to affix them to the bulbs as indicated in FIG. 3. As explained above, one of the support members 130 includes a connector 135 and comprises a printed circuit board. The other support member 120 may be comprised of the same materials or a different material. The configuration of the two support members, when disposed as shown in FIG. 3, provides a slot or channel defined by the sides of the L-shaped support members 120,130. The channel provides a space where the tubing 56,58 described above with reference to FIG. 1 may be safely disposed without interfering with the removal or either the array 100 or components within the chamber 52. As seen in FIGS. 5–6, the support members 120,130 also most preferably flare at their bottom ends 128,138 to help guide the array assembly 100 over the tubing 56,58 as the assembly is lowered into the radiation chamber 52.

Although certain preferred embodiments have been described herein with great detail, these embodiments are no meant to limit the present invention and are only provided for purposes of illustrating the invention. Upon review of the foregoing specification and drawings, those of skill in the art will realize that a number of adaptations, modifications and variations to the apparatus described above are readily made without departing from the basic concepts disclosed. Accordingly, reference should be made to the appended claims in order to determine the full scope of the present invention.

What is claimed is:

1. A system for separating and irradiating blood comprising: an instrument including a rotatable separation and irradiation chamber; and light array providing a source of radiant energy connected to the instrument and disposed within the separation and irradiation chamber, the light array comprising:

one or more bulbs each having a first end and a second end, and each comprising electrical connecting leads;

a first support member connected to the bulbs;

a second support member disposed between the first end and the second end, and connected to the bulbs, the support member further comprising a connector for receiving the electrical leads;

the support means define an end surface and an interior surface, wherein the support members are disposed adjacent the bulbs so the end surfaces are opposed to define a channel therebetween.

2. The system of claim 1, wherein the bulbs are attached to the support members using flexible self-locking straps.

3. The system of claim 1 comprising three bulbs.

4. The system of claim 1 comprising more than one bulb where the bulbs are held together by one or more straps.

5. The system of claim 1 wherein the second support member further comprises a circuit board and a microcircuit.

6. The system of claim 5 wherein the microcircuit comprises a clock/timer circuit for determining a total time of activation for the array, whereby upon reaching a predetermined bulb life value of the total time of activation, the clock/timer circuit disables the light array.

7. The system of claim 1 wherein the array is connected to the instrument by one or more spring mounts.

8. The system of claim 7 wherein the array is connected to the instrument by three centrally disposed and equally spaced spring mounts.

9. The system of claim 7 wherein the spring mounts comprise leaf springs.

10. A light array comprised of one or more tubular, circular bulbs each having a first end and a second end, and having one or more electrical leads attached to a support member disposed between the first and second ends, the support member comprising a connector for receiving the electrical leads, wherein the support member defines a channel.

11. The light array of claim 10 wherein the bulbs are attached to the support member with self-locking flexible straps.

12. The light array of claim 10 further comprising a second support member, the first and second support members each defining an end surface and an interior surface, wherein the support members are disposed adjacent the bulbs so the end surfaces are opposed to define a channel therebetween.

13. The light array of claim 10 wherein the support member further comprises a circuit board and a microcircuit.

14. The light array of claim 10 wherein the microcircuit comprises a clock/timer circuit for determining a total time of activation for the array, whereby upon reaching a predetermined bulb life value of the total time of activation, the clock/timer circuit disables the light array.

15. The light array of claim 10 comprising three bulbs.

16. The light array of claim 10 wherein the bulbs emit ultraviolet radiation.

17. A method of controlling the output of an array of bulbs comprising the steps of:

monitoring the total time the bulbs are activated; comparing the total time to a predetermined bulb life time value;

determining if the total time exceeds the predetermined bulb life time value;

disconnecting the array from a power source when the total time exceeds the predetermined bulb life time value; and replacing the array of bulbs.

\* \* \* \* \*